(12) United States Patent
Evers et al.

(10) Patent No.: US 9,052,300 B2
(45) Date of Patent: Jun. 9, 2015

(54) METHODS, SYSTEMS, AND APPARATUS TO DETERMINE A CLOT CARRYOUT CONDITION UPON PROBE RETRACTION DURING SAMPLE ASPIRATION AND DISPENSING

(76) Inventors: Alexander Vidlak Evers, Wilmington, DE (US); Bridgett Angela Harris, Elkton, MD (US); Alexander Openstone, Wilmington, DE (US); Jeffrey Kenneth Parmer, Newark, DE (US)

(*) Notice: Subject to any disclaimer, the term of this patent is extended or adjusted under 35 U.S.C. 154(b) by 330 days.

(21) Appl. No.: 13/522,632

(22) PCT Filed: Jan. 21, 2011

(86) PCT No.: PCT/US2011/022050
§ 371 (c)(1),
(2), (4) Date: Jul. 17, 2012

(87) PCT Pub. No.: WO2011/091245
PCT Pub. Date: Jul. 28, 2011

(65) Prior Publication Data
US 2012/0291532 A1   Nov. 22, 2012

Related U.S. Application Data

(60) Provisional application No. 61/297,379, filed on Jan. 22, 2010.

(51) Int. Cl.
G01N 35/10     (2006.01)
G01N 33/49     (2006.01)

(52) U.S. Cl.
CPC ........ G01N 35/1009 (2013.01); *G01N 33/4905* (2013.01); *G01N 2035/1018* (2013.01)

(58) Field of Classification Search
CPC .................................................. G01N 35/1009
See application file for complete search history.

(56) References Cited

U.S. PATENT DOCUMENTS 4,986,964 A    1/1991   Carr, Jr. et al.
5,441,892 A    8/1995   Baugh
(Continued)

FOREIGN PATENT DOCUMENTS

CN          101218493 A      7/2008
(Continued)

OTHER PUBLICATIONS

Machine translation of WO2008055757.*
Chinese Search Report of corresponding Chinese patent Application No. 201180006757.6, 2 pages.

*Primary Examiner* — Peter Macchiarolo
*Assistant Examiner* — Nathaniel Kolb
(74) *Attorney, Agent, or Firm* — Dugan & Dugan, PC

(57) ABSTRACT

A method of determining a condition of clot carryout from a sample container containing a sample fluid is disclosed. During aspiration of a fluid sample (e.g., blood), a level sensor, such as a capacitance sensor, is used to measure ascending and descending liquid level readings. A difference between the ascending and descending liquid level readings may be compared to a predetermined threshold. Non-ideal conditions, such as a clot carryout condition wherein a clot is carried out of the sample container on the exterior surface of the probe may be detected thereby. Systems and apparatus for carrying out the method are provided, as are other aspects.

17 Claims, 3 Drawing Sheets

(56) References Cited

U.S. PATENT DOCUMENTS

| | | | |
|---|---|---|---|
| 6,022,747 A | 2/2000 | Gherson et al. | |
| 6,158,269 A | 12/2000 | Dorenkott et al. | |
| 2007/0134131 A1* | 6/2007 | Watson et al. | 422/65 |
| 2010/0028213 A1* | 2/2010 | Gorka | 422/100 |

FOREIGN PATENT DOCUMENTS

| | | |
|---|---|---|
| WO | 2007/006903 A2 | 1/2007 |
| WO | 2008/055757 A1 | 5/2008 |
| WO | WO 2008055757 A1 * | 5/2008 |

\* cited by examiner

METHODS, SYSTEMS, AND APPARATUS TO DETERMINE A CLOT CARRYOUT CONDITION UPON PROBE RETRACTION DURING SAMPLE ASPIRATION AND DISPENSING

RELATED APPLICATIONS

This application claims priority to U.S. Provisional Application Ser. No. 61/297,379 entitled "Methods, Systems, and Apparatus to Determine A Clot Carryout Condition Upon Probe Retraction During Sample Aspiration and Dispensing" filed on Jan. 22, 2010, the disclosure of which is hereby incorporated by reference in its entirety herein.

FIELD OF THE INVENTION

The present invention relates generally to methods, systems, and apparatus for determining the presence of clots during aspiration and dispensing of samples in clinical analyzers.

BACKGROUND OF THE INVENTION

In testing within clinical laboratories to measure various chemical constituents of body fluids obtained from patients, such as whole blood, blood serum, blood plasma, and the like, automated clinical analyzers may reduce the number of trained technicians required to perform the analyses, improve accuracy of the testing, and reduce the cost per test.

Typically, an automated analyzer includes an automated sample fluid aspirating and dispensing system, which is adapted to aspirate a sample of body fluid from one sample container and dispense the body fluid sample into another reaction container (e.g., a cuvette). The sample body fluid aspirating and dispensing system typically includes a pipette (otherwise referred to as a "sample probe") mounted on a moveable arm, to perform the aspiration and dispensing functions.

One or more chemical reagents, which are specific to the test to be performed, may be disposed into the reaction container, thereby mixing the body fluid sample with the chemical reagent. By examining the reaction products resulting from mixing the body fluid sample and the reagent(s), the automated analyzer may determine a concentration of a specific chemical constituent contained therein. Upon completion of the testing, the automated analyzer may store or print the results of the test.

During the aspiration operation, the moveable arm, which may be under the control of a robotic controller, may position the sample probe above the sample container, and descend the probe into the container until the probe is partially immersed in the body fluid sample in the container. A pump or other aspirating device is then activated to draw (aspirate) a portion of the body fluid sample from the sample container into the probe. The probe is then ascended (retracted) from the sample container such that the body fluid sample may be transferred to the reaction container for testing. During the ascending step, sometimes clotted fluid (a clot, such as a fibrin clot) may be pulled (carried out) of the sample fluid on the probe. These types of clots carried out by the probe may be quite sizeable. In some instances, the clot may fall from the probe, and this may possibly contaminate the analyzer, areas around the analyzer, and/or possibly affect the test results of the sample being tested (or even other samples). Accordingly, the inventors recognized there is a need for determining such occurrences of clot carryout during probe ascending, such that the aforementioned problems may be avoided.

SUMMARY OF THE INVENTION

The present invention provides a method for detecting clots during aspiration and dispensing of a sample fluid. The method includes descending a sample probe into a sample container containing the sample fluid, measuring a first level reading during the descending, ascending the sample probe, measuring a second level reading during the ascending, and determining a clot carryout condition based upon the first level reading and the second level reading.

According to another aspect, the present invention provides a method for detecting clots during aspiration and dispensing of a sample fluid. The method includes descending a sample probe into a sample container containing the sample fluid, measuring a first capacitance reading during the descending, ascending the sample probe, measuring a second capacitance reading during the ascending, and determining a clot carryout condition based upon the first and second capacitance readings.

According to another aspect, the present invention provides a method for detecting clots during aspiration and dispensing of a sample fluid. The method includes providing a sample probe, descending the sample probe into a sample container containing a volume of the sample fluid, measuring a first capacitance reading during descending as the probe first contacts a surface of the sample fluid, drawing at least some of the sample fluid into the sample probe, determining the presence of a clot condition within the inner passage of the sample probe, ascending the sample probe, measuring a second capacitance reading during the ascending, and determining the presence of a clot carryout condition based on a difference between the first capacitance reading and the second capacitance reading, wherein the clot carryout condition is where a clot is carried out on an external surface of the sample probe.

According to another aspect, the present invention provides an aspirating and dispensing system. The system includes a sample probe, a robot component adapted to descend and ascend the sample probe into and out of a volume of sample fluid contained in a sample container, an aspirator adapted to draw the sample fluid into an inner passage of the sample probe, level sensing adapted to measure a descending liquid level during descending and an ascending liquid level during ascending, and clot carryout detection adapted to determine a presence of a clot carryout condition based on the descending and an ascending liquid levels, wherein the clot carryout condition is where a clot is carried out on an external surface of the sample probe.

According to another aspect, the present invention provides an aspirating and dispensing apparatus. The aspirating and dispensing apparatus includes a sample probe including a sensor, and a controller coupled to the sensor, the controller adapted to record a descending liquid level sensed by the sensor during descending, record an ascending liquid level sensed by the sensor during ascending, and determine a presence of a clot carryout condition based on the descending and ascending liquid levels, wherein the clot carryout condition is where a clot is carried out on an external surface of the sample probe.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

BRIEF DESCRIPTION OF THE DRAWINGS

The invention will be better understood by referring to the detailed description taken in conjunction with the following drawings.

DETAILED DESCRIPTION OF THE INVENTION

In view of the foregoing difficulties, there is an unmet need to reduce the propensity for carrying clots out of the sample container that have clung onto the outside of, or otherwise extend out of, the sample probe. To address this need, embodiments according to aspects of the present invention provide a method of detecting the presence of clot carryout condition upon retraction (ascending of the probe out of the sample container). The method includes a level detection function, which detects both a descending liquid level and an ascending liquid level. A difference between these liquid levels may be used to determine the presence of the clot carryout condition. In particular, a difference above a predetermined threshold value may be used to signal the presence of a clot carryout condition.

In some embodiments, capacitance readings may be used to determine the descending and ascending liquid levels. However, any method of level detection may be used with the present invention. In some embodiments, conventional clot detection may be used in conjunction with the clot carryout detection method of the present invention. In this manner, if a small clot is detected by a conventional clot detection method, then movement of the probe and the sample to a drain may be safely carried out, without fear of contaminating the analyzer or surroundings if the clot carryout detection of the present method determines that no clot carryout condition is present.

These and other aspects and features of the invention will be described with reference to FIGS. 1-3 herein.

Figure 1:
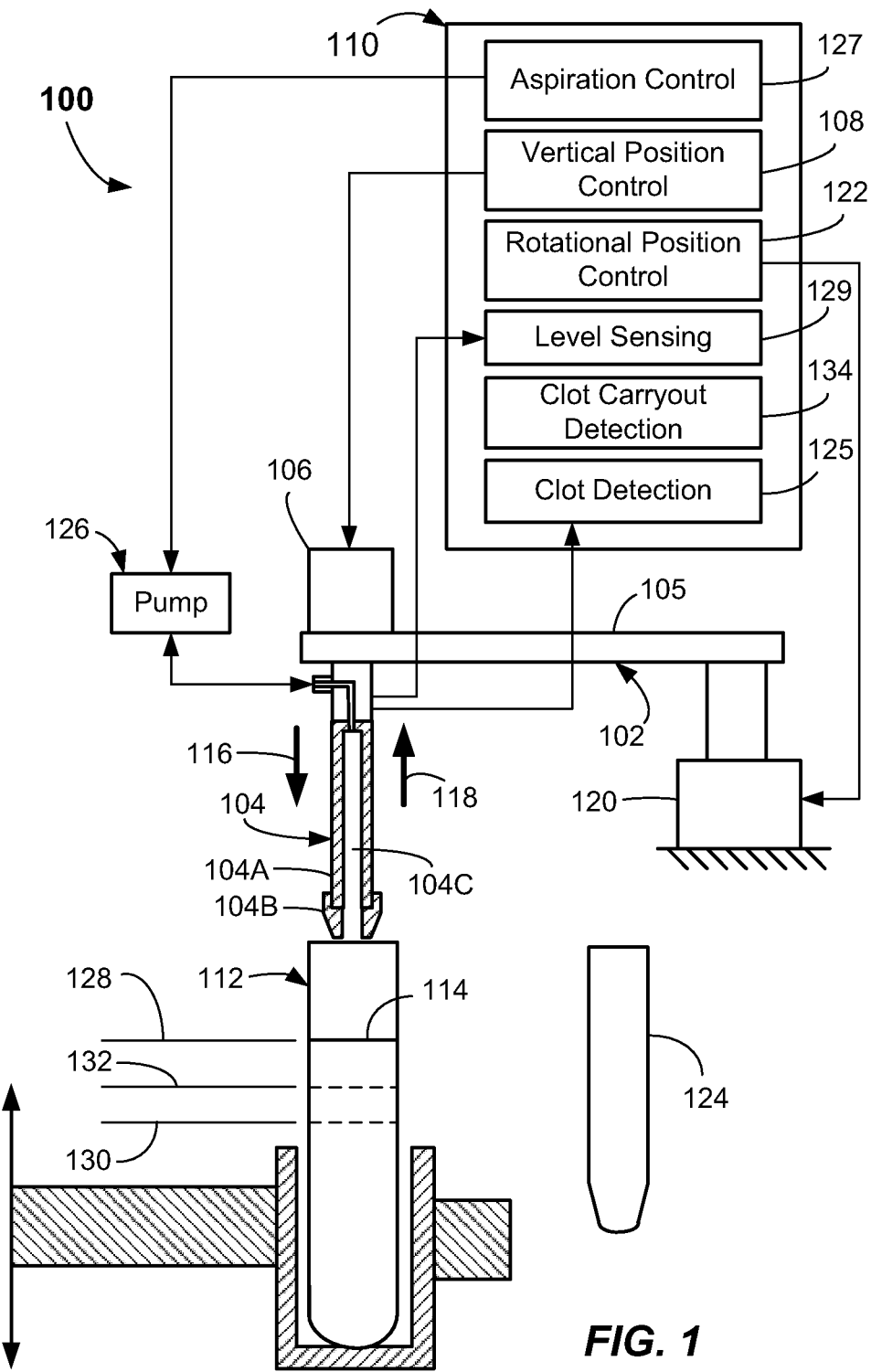
FIG. 1 is a schematic diagram of an aspirating and dispensing system according to the present invention.

Referring to FIG. 1, an aspirating and dispensing system 100 is illustrated. The aspirating and dispensing system 100 includes any suitable moving component(s) 102 for carrying out motion of a sample probe 104. The moving component 102 may include a robot component 105 (e.g., robot arm) to which the sample probe 104 may be mounted. The robot component 105 may swing about a fixed axis to provide horizontal motion capability, for example. Further, vertical motion of the sample probe 104 along a vertical axis may be imparted by a linear actuator 106 of the moveable component(s) 102, which may be coupled to the probe 104.

The linear actuator 106 may be actuated by a vertical position control 108 of a controller 110. The actuator 106 may be operable to descend and ascend the sample probe 104 into and out of a sample container 112 containing a volume of a sample fluid 114, at least some of which is to be tested. In particular, the sample probe 104 may be actuated along the directions indicated by arrow 116 (descending the probe 104) and arrow 118 (ascending or retracting of the probe 104).

Additionally, the moving component(s) 102 may include a rotational actuator 120, which may be controlled by rotational position control 122 of the controller 110 to rotate the moving component(s) 102 and sample probe 104 along a horizontal (e.g., an arcuate path) from a position above the sample container 112 to a position above a reaction container 124 (e.g., a cuvette). Other types of components for imparting vertical motion may be used. For example, the rotational actuator 120 may also include vertical motion capability. Similarly, a gantry system may be employed wherein the probe 104 may be attached to a beam of a gantry moveable in the vertical and horizontal directions.

An aspirator 126, such as a pump, may be coupled, such as by a section of hollow tube or conduit, to the sample probe 104 to allow a suitable amount of the sample fluid 114 to be drawn into the inner passage 104C of the sample probe 104 for testing. Aspirator 126 may also have other functions, such as aspirating and dispensing reagent and/or diluting materials, and may also dispense rinsing fluids. Aspiration control 127 of the controller 110 may be adapted, and operational, to control a level of pressure to draw in a desired amount of the sample fluid 114 into the probe 104, and also to control the dispensing operations performed by the aspiration and dispensing system 100. The aspirator 126 may include suitable pressure sensor(s), valve(s), accumulator(s), or other pneumatic or hydraulic components (not shown) to effectuate the fluid drawing action. Any suitable apparatus for drawing the fluid into the probe 104 may be used. For example, aspirating and dispensing systems, which may be used with the present invention, are described in U.S. Pat. Nos. 7,634,378; 7,477,997; and 7,150,190, which are hereby incorporated by reference herein.

Typically, the sample probe 104 includes a probe body 104A and a probe tip 104B. The tip 104B may be disposable and removably coupled to the probe body 104A. A supply of tips 104B may be stored nearby where they may be accessed by the probe body 104A upon movement by the robot component 102. However, in some applications, a non-disposable tip permanently secured to the probe body 104A may be used. In this instance, a washing and rinsing station may be located within the reach of the robot component 102. The probe 104 includes the inner passage 104C into which at least a portion of the sample fluid 114 is drawn.

In some embodiments, the aspiration and dispensing system 100 may include additional components/systems, such as clot detection 125 adapted to sense the presence of a clot within the passage 104C of the probe 104. For example, pressure (as measured by a pressure sensor coupled to the probe passage 104C—not shown) may be sensed to determine the presence of a clot, such as is described in U.S. Pat. No. 7,477,997, which is hereby incorporated by reference herein. Any conventional clot detection method may be used.

In operation, during aspiration, the robot component(s) 102 position the sample probe 104, with a probe tip 104B attached, above the sample container 112 and descends the sample probe 104 at a predetermined rate along the descending direction 116. The descent into the container 112 is produced by the action of the linear actuator 106 under the control of the vertical position control 108 until the probe 104 reaches the surface of the sample fluid 114 therein. When the probe 104 touches the fluid surface, level sensing 129, which may be provided by a capacitance detection circuit, determines that the surface of the sample 114 has been reached. For example, the capacitance detection circuit may detect the surface by detecting an initial step change in a measured capacitance, which is above a threshold value. Once the fluid surface is detected, the vertical position control 108 records a vertical position of the sample probe 104 when first contacting the surface as the "descending liquid level" illustrated by line 128. The vertical position control 108 may control the linear actuator 106 to continue the descent along direction 116 to a predetermined level 130 (illustrated by the lower dotted line), which is below the descending liquid level 128. Capacitance liquid level measuring is described, for example, in U.S. Pat. No. 7,150,190, which is hereby incorporated by reference herein. Other types of level detection may be employed.

Now the aspirator 126 may be operated via aspiration control 127 to draw off a predefined volume of the fluid sample 114 into the inner passage 104C of the sample probe 104. As the pump 126 is operated, the level of sample fluid 114 in the sample container 114 is drawn down, i.e., lowered. When a desired amount of sample fluid 114 has been received within the sample probe 104, as measured by aspiration control 127, the pump 126 may be stopped such that no further aspiration of the sample fluid 114 occurs.

After the desired volume of sample fluid 114 has been aspirated into the probe 104, the sample probe 104 is ascended along arrow 118 to retract the probe 104 from the sample container 112, such that a portion of the sample 114 may be transferred to the reaction container 124. As the probe ascends along direction 118, level sensing 129 again may sense a step change in capacitance above a predetermined threshold level. This second step change, when detected, may be recorded as the "ascending liquid level" and is designated as 132 (the upper dotted line).

Of course, in the absence of a clot carryout condition, i.e., adhering of a clot to the outside surface of the probe or otherwise extending out of the passage 104C of the probe 104, the second level 132 may be roughly determinable. In the absence of a clot being carried, the level is based upon the initial level, the volume of fluid displaced as the sample probe 104 is submerged into the fluid to the desired depth, and the volume of fluid aspirated from the sample container 112 based upon knowing the pressure and exact dimensions of the probe 104. However, surface tension effects will cause the ascending liquid level to be measured as slightly higher than the rough calculations would indicate, because the sample fluid 114 adheres or clings via surface tension to the surface of the probe 104. However for a non-clotted sample, the ascending liquid level 132 can be determined experimentally and used in the method as will be described herein. For example, the average ascending level may be determined experimentally by averaging a number of aspirations that are known to be free of clot carryout conditions.

In the event that the clot detection 125 detects conditions that indicate the possible or likely presence of a clot in the aspirated sample within the inner passage 104C, then the recorded values of the descending liquid level 128 and the ascending liquid level 132 may be further utilized. The levels 128,132 may be used to determine if a clot is being carried out of the sample container by the probe 104 (to determine a "clot carryout condition"). The clot detection 125 may be accomplished by any suitable method, such as described in U.S. Pat. Nos. 7,867,769, 7,634,378; 7,477,997; 6,119,533; 6,060,320; and 6,022,747.

According to the invention, the presence of a clot carryout condition is determined by clot carryout detection 134 based on the recorded descending liquid level 128 and the recorded ascending liquid level 132. In particular, the presence of a clot carryout condition may be determined based upon a difference between the recorded descending liquid level 128 and the recorded ascending liquid level 132. If the difference is above (greater than) a predetermined threshold value, then clot carryout detection 134 may determine that a clot carryout condition is present, i.e., a mass of a clotted sample material (e.g., a fibrin clot) may be adhered to or otherwise connected to, or hanging from, the sample probe 104. Accordingly, upon a determination of a clot carryout condition being present, corrective measures may be undertaken by the vertical and rotational controls 108, 122. For example, the vertical and rotational controls, 108, 122 may simply halt or stop any further motion of the probe 104. This may allow appropriate remedial measures (as discussed below) to take place. The predetermined difference between the descending and ascending liquid levels 128, 132 may be set to be about 1.5 or more times, about 2 or more times, about 3 or more times, or even 4 or more times an expected difference between the descending liquid level and the ascending liquid level established for un-clotted sample materials. The expected difference value may be determined experimentally through averaging a series of tests and determinations of the descending and ascending liquid level readings where no clotting is apparent.

Remedial measures may include stopping further vertical motion of the probe 104 along direction 118, operator intervention, wash or rinse in place (without moving), or preliminary wash or rinse followed by moving the probe 104 to a wash area or station where additional wash or rinse steps may be accomplished. Stopping the probe 104 when a clot carryout condition is detected by clot carryout detection 134 may prevent a clot from ever leaving the confines of the sample container 112, or if the clot should drop from the sample probe 104 it may fall directly into the sample container 112. Accordingly, instances of contamination of the clinical analyzer, its surroundings, and/or other samples and instances of analyzer downtime may possibly be avoided by utilizing the present invention.

Figure 2:
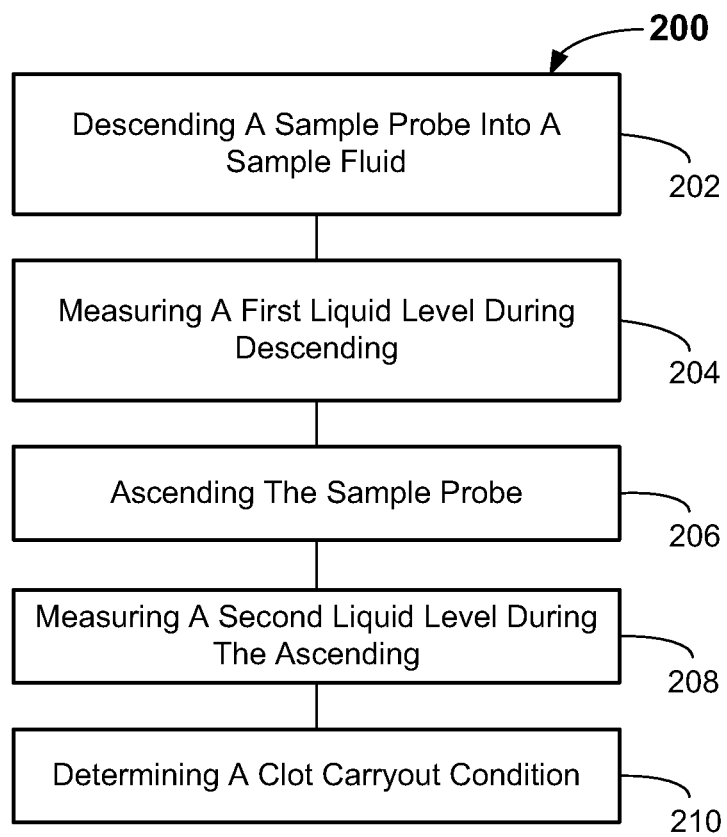
FIG. 2 is a flow chart illustrating methods according to embodiments of the present invention.
Figure 3:
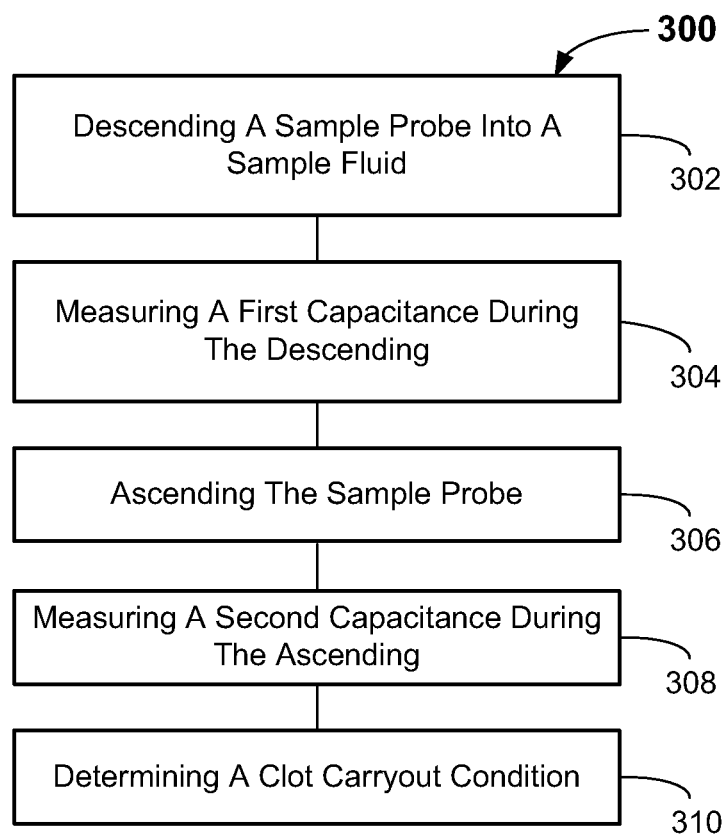
FIG. 3 is another flow chart illustrating methods according to embodiments of the present invention.

Referring now to FIG. 2, a broad method of the invention is illustrated. The method 200 is adapted to detect a clot carryout condition during aspiration and dispensing of a sample fluid. According to embodiments, the method 200 includes, in 202, descending a sample probe (e.g., sample probe 104) into a sample container (e.g., sample container 112) containing the sample fluid (e.g., sample fluid 114). This is followed by measuring a first liquid level (e.g., descending level 128) reading during the descending, in 204. After a suitably-sized portion of the sample fluid has been aspirated via the action of the aspirator (e.g., aspirator 126), the sample probe may be ascended in 206, such as under the action of the vertical position control 108 (See FIG. 1). A second liquid level reading (e.g., ascending level 132) is measured during the ascending, in 208. Finally, in 210, the presence or absence of a clot carryout condition is determined. According to embodiments, the presence or absence may be determined based upon a difference between the first and second liquid level readings (e.g., difference between the descending level 128 and the ascending level 132). In particular, if the difference is above a predetermined threshold value, a clot carryout condition is determined. Accordingly, remedial measures may be undertaken, such as described above. If no clot carryout condition is determined, i.e., the difference is below the threshold, then the system 100 (See FIG. 1) may continue with dispensing the fluid sample into the reaction container 124 (e.g., a cuvette) for testing, followed by movement to a drain station at another location, possibly followed by wash and/or rinse steps.

In accordance with some embodiments of the invention, a method for detecting clots during aspiration and dispensing of sample fluid wherein the level sensing is accomplished by measuring capacitance is provided. The method 300, as illustrated in FIG. 3, may include, in 302, descending a sample probe (e.g., sample probe 104) into a sample container (e.g., sample container 112) containing a sample fluid (e.g., 114), followed by measuring a first capacitance reading during the descending, in 304. The first capacitance reading is determined by a jump in capacitance measured by the level detection 129 when the probe first touches the surface of the sample fluid 112. Following aspiration of a suitable portion of the sample fluid by the action of an aspirator 126 and aspiration control 127, the sample probe 104 (See FIG. 1) is ascended, in 306. A second capacitance reading is measured during the ascending, in 308, by the level detection 129. The second level is determined by another jump in the capacitance as the probe (or clot) separates from the surface of the fluid sample. Following the level sensing, a clot carryout condition is determined in 310 by clot carryout detection algorithm. The clot carryout condition, as described above, may be based upon the first and second capacitance readings. In particular, a difference between the measured capacitance levels may be measured. If that difference is above a predetermined threshold value, then a clot carryout condition is determined, and remedial measures, as discussed above, may be undertaken.

Having shown the preferred embodiment, those skilled in the art will realize many variations are possible that will still be within the scope and spirit of the claimed invention. Therefore, it is the intention to limit the invention only as indicated by the scope of the claims.

What is claimed is:

1. A method for detecting clots during aspiration and dispensing of sample fluid, comprising:
    descending a sample probe into a sample container containing the sample fluid;
    measuring a first level reading during the descending;
    ascending the sample probe;
    aspirating at least a portion of the sample fluid, and detecting a presence of a clot condition in an inner passage of the sample probe;
    measuring a second level reading during the ascending; and
    determining a clot carryout condition on an exterior of the probe based upon the first level reading and the second level reading
    wherein upon determining the clot carryout condition exists, the ascending movement of the sample probe is stopped to prevent contamination by preventing a clot from leaving the confines of the sample container.

2. The method of claim 1, wherein the presence of a clot carryout condition is based upon a difference between the first level reading and the second level reading.

3. The method of claim 2, wherein the presence of a clot carryout condition is based upon the difference being greater than a predetermined threshold value.

4. The method of claim 3, wherein the predetermined threshold value is 1.5 or more times an expected difference between a descending liquid level and an ascending liquid level established for un-clotted sample materials.

5. A method for detecting clots during aspiration and dispensing of sample fluid, comprising:
    descending a sample probe into a sample container containing the sample fluid;
    measuring a first capacitance reading during the descending;
    aspirating at least a portion of the sample fluid, and detecting a presence of a clot condition in an inner passage of the sample probe;
    ascending the sample probe;
    measuring a second capacitance reading during the ascending; and
    determining a clot carryout condition based upon the first and second capacitance readings
    wherein upon determining the clot carryout condition exists, the ascending movement of the sample probe is stopped to prevent contamination by preventing a clot from leaving the confines of the sample container.

6. The method of claim 5, wherein the presence of a clot carryout condition is based upon a difference between the first and second capacitance readings.

7. The method of claim 6, wherein the presence of a clot carryout condition is based upon the difference being greater than a predetermined threshold value.

8. The method of claim 5, wherein
    if the clot carryout condition exists, then then the ascending of the sample probe is stopped, and
    if the clot is detected in the inner passage, but no clot carryout condition exists, then then the ascending of the sample probe is not stopped.

9. The method of claim 5, wherein
    if the clot carryout condition exists, then then the ascending of the sample probe is stopped, and
    a wash or rinse in place is carried out.

10. A method for detecting clots during aspiration and dispensing of sample fluid, comprising:
    descending a sample probe into a sample container containing the sample fluid;
    measuring a first capacitance reading during the descending;
    aspirating at least a portion of the sample fluid, and detecting a presence of a clot condition in the inner passage of the sample probe;
    ascending the sample probe;
    measuring a second capacitance reading during the ascending;
    determining a clot carryout condition based upon the first capacitance reading and the second capacitance reading, wherein if the clot is detected in the inner passage of the sample probe, and the difference between the first capacitance reading and the second capacitance reading is below a predetermined threshold value, then the movement of the sample probe is not stopped.

11. A method for detecting clots during aspiration and dispensing of sample fluid, comprising:
    providing a sample probe;
    descending the sample probe into a sample container containing a volume of the sample fluid;
    measuring a first capacitance reading during descending as the probe first contacts a surface of the sample fluid;
    drawing at least some of the sample fluid into the sample probe;
    determining a presence of a clot condition within an inner passage of the sample probe;
    ascending the sample probe;
    measuring a second capacitance reading during the ascending; and determining a presence of a clot carryout condition based on a difference between the first capacitance reading and the second capacitance reading, wherein the clot carryout condition is where a clot is carried out on an external surface of the sample probe
    wherein upon determining the clot carryout condition exists, the ascending movement of the sample probe is stopped to prevent contamination by preventing a clot from leaving the confines of the sample container.

12. An aspirating and dispensing system, comprising:
a sample probe;
a robot component adapted to descend and ascend the sample probe into and out of a volume of sample fluid contained in a sample container;
an aspirator adapted to draw the sample fluid into an inner passage of the sample probe;
level sensing adapted to measure a descending liquid level during descending and an ascending liquid level during ascending;
clot detection adapted to determine a presence of a clot condition in an inner passage of the sample probe upon drawing the sample fluid into the inner passage; and
clot carryout detection adapted to determine a presence of a clot carryout condition based on the descending and ascending liquid levels, wherein the clot carryout condition is where a clot is carried out on an external surface of the sample probe
wherein upon determining the clot carryout condition exists, the ascending movement of the sample probe is stopped to prevent contamination by preventing a clot from leaving the confines of the sample container.

13. The aspirating and dispensing system of claim 12, further comprising a controller adapted to determine an existence of the clot carryout condition.

14. The aspirating and dispensing system of claim 13, further comprising a controller adapted to control a position of the robot component based upon an existence of the clot carryout condition.

15. The aspirating and dispensing system of claim 12, wherein the level sensing is adapted to measure a change in capacitance.

16. The aspirating and dispensing system of claim 12, wherein the clot carryout detection is adapted to determine a presence of a clot carryout condition based on a difference between the descending and ascending liquid levels.

17. An aspirating and dispensing apparatus, comprising:
a sample probe including a sensor, the sample probe including an inner passage and an external surface; and
a controller coupled to the sensor, the controller adapted to
record a descending liquid level sensed by the sensor during descending,
record an ascending liquid level sensed by the sensor during ascending,
detecting a presence of a clot condition within an inner passage of the sample probe upon aspirating a sample fluid,
determine a presence of a clot carryout condition based on the descending and ascending liquid levels, wherein the clot carryout condition is where a clot is carried out on an external surface of the sample probe
stop ascending if a clot carryout condition is determined.

* * * * *